United States Patent
Mallya et al.

(10) Patent No.: US 7,310,435 B2
(45) Date of Patent: Dec. 18, 2007

(54) METHOD AND APPARATUS FOR EXTRACTING MULTI-DIMENSIONAL STRUCTURES USING DYNAMIC CONSTRAINTS

(75) Inventors: Yogisha Mallya, Karnataka (IN); Rakesh Mullick, Karnataka (IN); Srikanth Suryanarayanan, Karnataka (IN)

(73) Assignee: General Electric Company, Niskayuna, NY (US)

( * ) Notice: Subject to any disclaimer, the term of this patent is extended or adjusted under 35 U.S.C. 154(b) by 793 days.

(21) Appl. No.: 10/723,411

(22) Filed: Nov. 25, 2003

(65) Prior Publication Data

US 2005/0111732 A1 May 26, 2005

(51) Int. Cl.
*G06K 9/00* (2006.01)

(52) U.S. Cl. ............ 382/128; 382/154; 378/23

(58) Field of Classification Search ............ 382/109, 382/128, 129, 130, 131–133, 154, 168, 172–173, 382/194, 199, 203, 209, 254, 257, 274, 276, 382/316; 600/425, 410; 378/21, 23
See application file for complete search history.

(56) References Cited

U.S. PATENT DOCUMENTS

| | | | | |
|---|---|---|---|---|
| 5,273,040 A | * | 12/1993 | Apicella et al. | 600/410 |
| 5,570,404 A | | 10/1996 | Liang et al. | 378/8 |
| 5,832,134 A | * | 11/1998 | Avinash et al. | 382/257 |
| 6,408,201 B1 | * | 6/2002 | Foo et al. | 600/410 |
| 6,842,638 B1 | * | 1/2005 | Suri et al. | 600/425 |
| 7,024,021 B2 | * | 4/2006 | Dunn et al. | 382/109 |
| 7,103,204 B1 | * | 9/2006 | Celler et al. | 382/131 |
| 2002/0054707 A1 | | 5/2002 | Florent et al. | |
| 2003/0053697 A1 | | 3/2003 | Aylward et al. | |

FOREIGN PATENT DOCUMENTS

WO    WO02/22013    3/2002

OTHER PUBLICATIONS

XP000636816, "Frequency Analysis of Gradient Estimators in Volume Rendering", Mark J. Bentum et al., IEEE Transactions on Visualization and Computer Graphics, vol. 2, No. 3, Sep. 1996, pp. 242-253.

XP000637134, "A 3D Surface Tracking Algorithm", Xiaooing Qu et al., Computer Vision and Image Understanding, vol. 64, No. 1, Jul. 1996, pp. 147-156.

"Surface Shading in Tomographic VolumeVisualization: A Comparative Study", A. Pommert et al., IEEE, 1990, pp. 19-26.

(Continued)

*Primary Examiner*—Azarian Seyed
(74) *Attorney, Agent, or Firm*—Jean K. Testa; Curtis B. Brueske

(57) ABSTRACT

A technique is provided for segmenting a structure of interest from a volume dataset. The technique identifies regions of the structure using templates having characteristics of the structure of interest. The identified regions may then undergo a constrained growth process using dynamic constraints that may vary based on local statistics associated with the identified structure regions. Edges within the volume may be determined using gradient data determined by evaluating the strongest gradient between each pixel and all adjacent pixels. The edge data may be used to prevent the constrained growing process from exceeding the boundaries of the structure of interest.

27 Claims, 3 Drawing Sheets

OTHER PUBLICATIONS

French Preliminary Search Report—Nov. 25, 2005.

Adams, Rolf, et al., Seeded Region Growing, IEEE Transactions on Pattern Analysis and Machine Intelligence, pp. 641-647, 1994.

Alyassin, Abdalmajeid M., et al., Semi-automatic Bone Removal Technique from CT Angiographic Data, Proceedings of the SPIE—The International Society for Optical Engineering 2000, General Electric Research & Development Center, GE Medical Systems (2004).

Hojjatoleslami, S. A., et al., Region Growing: A New Approach, IEEE Transactions on Image Processing, pp. 1079-1084, 1998.

Kass, Michael, et al., Snakes: Active Contour Models, International Journal of Computer Vision, 1 (1987) 321-331.

Mullick, Rakesh, Method and Apparatus for Removing Obstructing Structures in CT, U.S. Appl. No. 10/301,018, filed Nov. 21, 2002, General Electric Company.

Subramanyan, Krishna, Vessel Tracking and Tree Extraction Method and Apparatus, PCT application, International Publication No. WO 03/046835 A1, IP Publication date Jun. 5, 2003.

Wink, O., et al., Fast Delineation and Visualization of Vessels in 3-D Angiographic Images, IEEE Transactions on Medical Imaging, vol. 19, No. 4, Apr. 2000.

Xu, Chenyang, et al., Snakes, Shapes, and Gradient Vector Flow, IEEE Transactions on Image Processing, vol. 7, No. 3, Mar. 1998, pp. 359-369.

Yim, Peter J., et al., Vessel Surface Reconstruction with A Tubular Deformable ModelDec. 2001.

* cited by examiner

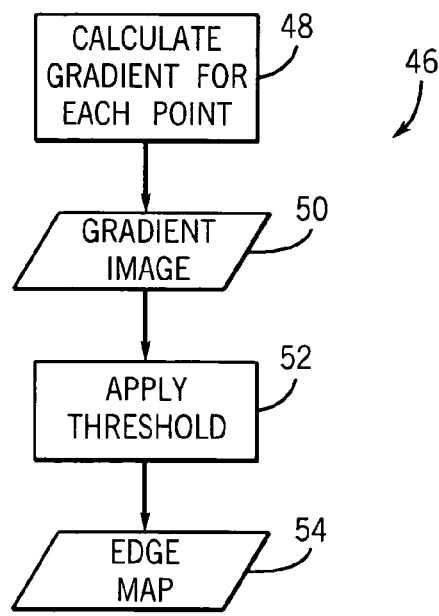
FIG. 3
FIG. 4
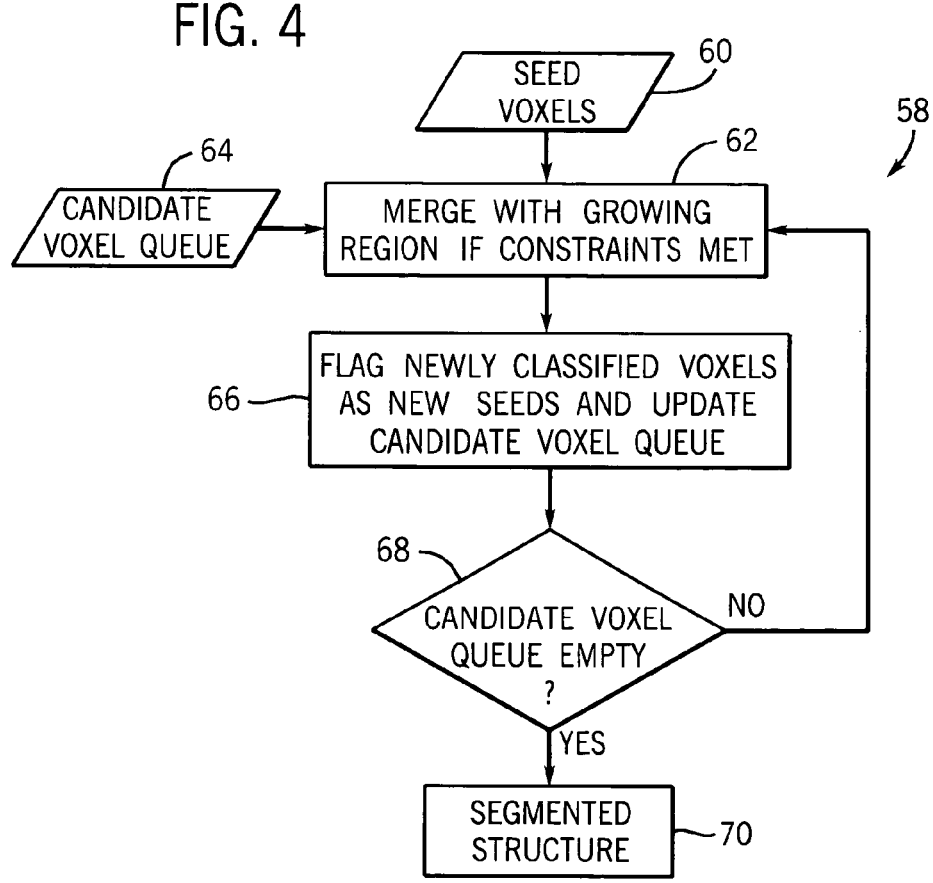

METHOD AND APPARATUS FOR EXTRACTING MULTI-DIMENSIONAL STRUCTURES USING DYNAMIC CONSTRAINTS

BACKGROUND OF THE INVENTION

The present invention relates generally to the field of medical imaging. Specifically, the invention relates to a technique for automatically extracting structures, particularly three-dimensional structures, from a volume dataset.

A volume dataset may be generated by a variety of medical imaging technologies or modalities. For example, magnetic resonance imaging (MRI) modalities generate volume datasets by exposing a patient to magnetic field and by measuring the response and realignment of various magnetically susceptible molecule types within the body. By imposing weak gradient fields along the three-dimensional axes during the process, positional information may be obtained which allows a volume dataset to be constructed. Other technologies, such computed tomography (CT), measure the attenuation of streams of radiation through the body from numerous angles. The attenuation information may be combined and reconstructed to generate a volume dataset. Still other imaging modalities, such as various nuclear imaging technologies, measure the detectable emissions generated by labeled molecules, such as radionuclides or radiopharmaceuticals, to provide volume data. Though the manner in which a volume dataset is created may vary, with the above techniques representing only a sample, the analysis of volume datasets raise many common issues.

For instance, it is often desirable to segment and extract image data corresponding to contiguous and/or complex structures from the background volume for analysis. For example, in the field of CT angiography (CTA), the vascular and other circulatory system structures may be imaged, typically by administration of a radio-opaque dye prior to imaging. Visualization of the CTA data typically is performed in a two-dimensional manner, i.e., slice-by-slice, or in a three-dimensional manner, i.e., volume visualization, which allows the data to be analyzed for vascular pathologies. For example, the data may be analyzed for aneurysms, vascular calcification, renal donor assessment, stent placement, vascular blockage, and vascular evaluation for sizing and/or runoff. Once a pathology is located, quantitative assessments of the pathology may be made of the on the original two-dimensional slices.

As one might expect, segmentation and extraction of complex structures, such as the vasculature in the preceding CTA example, may benefit from accurate segmentation, i.e., identification, of the image data corresponding to the structure of interest. Similarly, quantitative assessment of located pathologies, as noted above, may also benefit from accurate segmentation. Existing segmentation techniques, however, may incorrectly incorporate background or proximate objects into the segmented structure due to poor recognition of edges or non-homogeneities in the image data. Similarly, existing techniques may improperly exclude image data from the segmented structure due to poor edge recognition and/or non-homogeneities. Such exclusions may potentially result in early or erroneous termination of the segmentation technique. Furthermore, splits or mergers in the structure of interest may not be properly segmented by existing techniques due to these shortcomings. In addition, anatomic and pathological variability within the patient population, such as due to plaque deposits in the vasculature or to the presence of interventional devices, such as stents, may further confound the segmentation process.

For example, in CTA, overlapping image intensities, close proximity of imaged structures, and limited detector resolution may make the automated separation of bone and vascular structures difficult. In particular, the proximity of vascular structures and bone in the head and neck region, along the vertebra and near the pelvis make segmentation an exceedingly complex task for computer-based algorithms. The presence of calcification or interventional devices may compound these difficulties.

As a result, proper segmentation of a complex or contiguous three-dimensional structure, such as the vasculature around the head and neck region, may require operator intervention or input. In particular, operator intervention may be needed to designate initial start points and/or to prevent the inadvertent inclusion or exclusions of volume data from the segmented structure. This operator intervention can lead to undesirable delays as well as to inter- and intra-user variability in the segmentation of structures. There is a need therefore, for an improved technique for segmenting structure in a volume, preferably with little or no human intervention.

BRIEF DESCRIPTION OF THE INVENTION

The present technique provides a novel approach to automatically segmenting a structure of interest in a volume data set. Automatic initialization may be performed to identify one or more initiation regions in the image data based upon templates that characterize properties of the structure of interest. The identified regions serve as starting points for the subsequent constrained growth process. Edge boundaries may be computed based on gradient data obtained by comparing each voxel to all adjacent voxels and assigning the maximum absolute gradient value as the gradient for the pixel. Constrained path finding may then be employed using the edge data and the initiation regions, as well as cross-sectional areas for regions in the image data. The constrained path finding process may employ dynamic constraints which are modified based upon local statistics, allowing candidate pixels to be selectively merged into the foreground region. The process may be iterated until the supply of candidate pixels is exhausted. The resulting volume comprises the segmented structure of interest.

In accordance with a first aspect of the technique, a method for determining edge voxels is provided. According to this aspect, a gradient for each of a plurality of voxels is calculated by determining a maximum absolute gradient component relative to each adjacent voxel. One or more edge voxels from the plurality of voxels is identified based upon a comparison of the gradients of each of the plurality of voxels to a threshold edge gradient. Systems and computer programs that afford functionality of the type defined by such methods are also provided by the present technique.

In accordance with another aspect of the present technique, a method for segmenting a structure is provided. According to this aspect, one or more candidate voxels are iteratively merged into a foreground region comprising at least one or more seed voxels. The candidate voxels are merged based on one or more dynamic constraints. The merged candidate voxels become the seed voxels for the next iteration. A queue of candidate voxels is iteratively updated each iteration based upon the new seed voxels. The iterative processes are terminated to generate a segmented structure comprising the foreground region. Systems and computer programs that afford functionality of the type defined by such methods are also provided by the present technique.

In accordance with a further aspect of the present technique, a method for identifying a structure of interest is provided. According to this aspect, at least one of a geometrical template and a functional template is provided. Each template represents at least one characteristic of a structure of interest. One or more regions of the structure of interest are identified based upon the similarity of the respective characteristic in the regions and the provided templates. Systems and computer programs that afford functionality of the type defined by such methods are also provided by the present technique.

In accordance with an additional aspect of the present technique, a method for automatically segmenting a structure from a set of image data is provided. According to this aspect, one or more initial regions corresponding to a structure of interest are selected from a volume data set. An edge map is generated from the volume data set. The structure of interest is iteratively segmented using at least the one or more initial regions and the edge map. The segmentation is based upon one or more dynamic constraints. Systems and computer programs that afford functionality of the type defined by such methods are also provided by the present technique.

BRIEF DESCRIPTION OF THE DRAWINGS

The foregoing and other advantages and features of the invention will become apparent upon reading the following detailed description and upon reference to the drawings in which:

FIG. 3 is a flowchart depicting a technique for calculating an edge map, in accordance with the present technique; and FIG. 4 is a flowchart depicting a technique for dynamically growing a segmented structure from a set of seed voxels, in accordance with the present technique.

DETAILED DESCRIPTION OF SPECIFIC EMBODIMENTS

Figure 1:
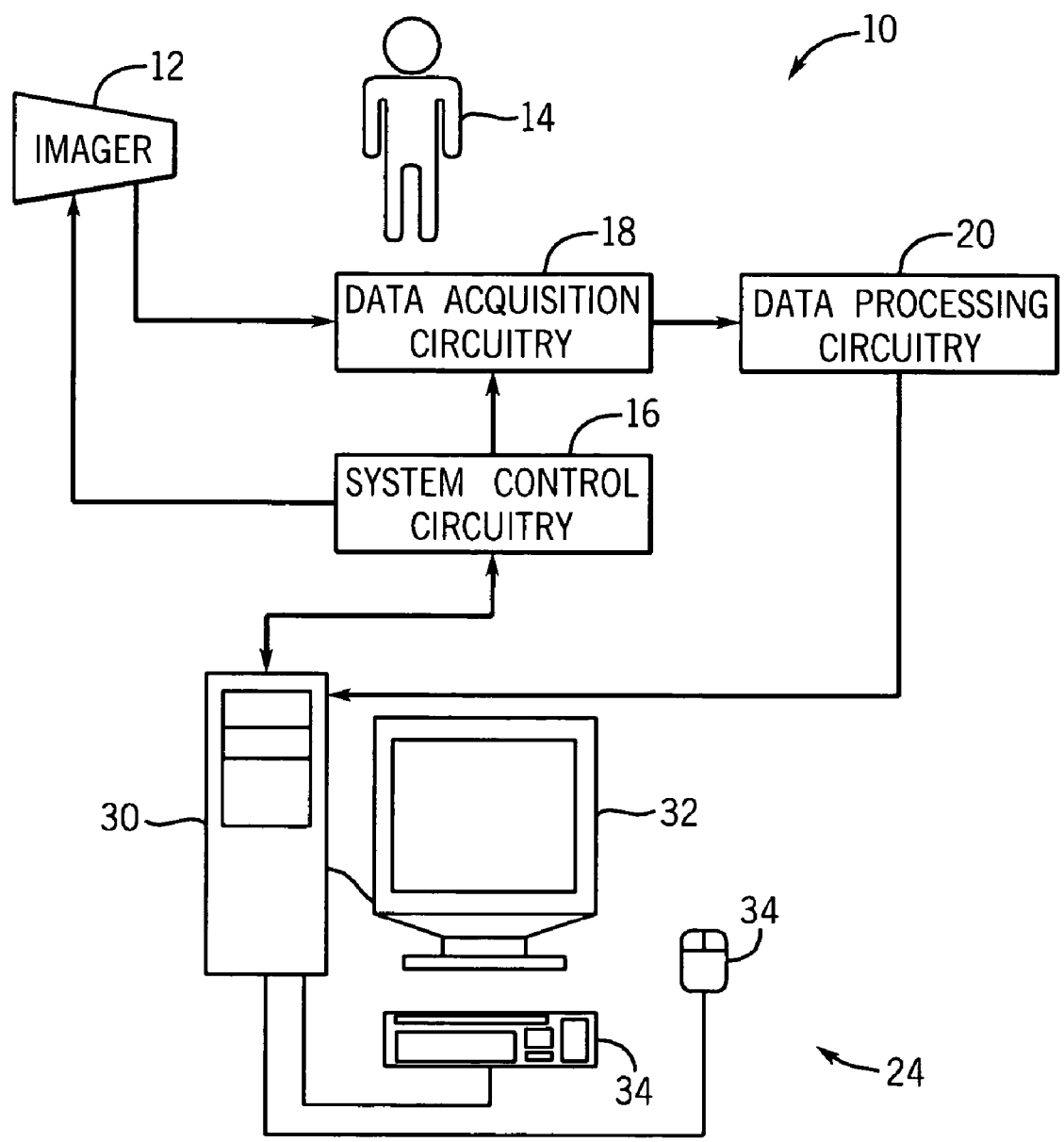
FIG. 1 is a general diagrammatical representation of certain functional components of an exemplary generic imaging system configured for remote operation via the present technique.

Turning now to the drawings, and referring first to FIG. 1, an exemplary imaging system 10 suitable for use in a medical context is depicted. Generally, the imaging system 10 includes some type of imager 12 that may operate in accordance with various physical principles for creating image data. In general, the imager 12 creates image data representative of regions of interest in a patient 14 in a digital medium. As will be appreciated by one of ordinary skill in the art, the imaging system 10 may comprise a computer tomography (CT), a magnetic resonance (MR), a positron emission tomography (PET), an electron beam tomography (EBT) or other modality of imaging system capable of generating a volume data set.

The imager 12 operates under the control of system control circuitry 16. The system control circuitry 16 may include a wide range of circuits, such as radiation source control circuits, timing circuits, circuits for coordinating data acquisition in conjunction with patient or table movements, circuits for controlling the position of radiation sources and detectors, and so forth. In the present context, the system control circuitry 16 may also include memory elements for storing programs and routines implementing the techniques described herein which may be executed by the system control circuitry 16 or by associated components of the imaging system 10.

The imager 12, following acquisition of the image data or signals, may process the signals, such as for conversion to digital values, and forward the image data to data acquisition circuitry 18. For digital systems, the data acquisition circuitry 18 may perform a wide range of initial processing functions, such as adjustment of digital dynamic ranges, smoothing or sharpening of data, as well as compiling of data streams and files, where desired. The data may then be transferred to data processing circuitry 20 where additional processing and analysis are performed. For the various digital imaging systems available, the data processing circuitry 20 perform substantial analyses of data, ordering of data, sharpening, smoothing, feature recognition, and so forth, which facilitate the generation of a useful set of image data. The data processing functions may be performed, in general, under the guidance of one or more technologists. The acquired images or image data may be stored in short or long-term storage devices, such as a picture archiving communication system (PACS) that may be accessible locally or over a network.

The above-described operations and functions of the imaging system 10 may be controlled by a scanner console 24, which typically interfaces with the system control circuitry 16. The scanner console 24 may include one or more general purpose or application specific computers 30 or processor-based components. The scanner console 24 may include a monitor 32 or other visual display and one or more input devices 34. The monitor 32 and input devices 34 may be used for viewing and inputting configuration information or for operating aspects of the imaging system 10, in accordance with the techniques discussed herein. As with the system control circuitry 16, the scanner console 24 may comprise or communicate with a memory or data storage component for storing programs and routines implementing the techniques described herein. Moreover, the memory or storage component may comprise one or more memory devices, such as magnetic or optical drives, of similar or different types, which may be local or remote from one another.

The scanner console 24 may be coupled to a picture archiving and communications system (PACS). The PACS may be coupled to a remote console, radiology department information system (RIS), hospital information system (HIS) or to an internal or external network, so that others at different locations may gain access to the image and to the image data. Furthermore, more than one scanner console 24 may be provided locally. For example, an imaging scanner or station may include a console which permits regulation of the parameters involved in the image data acquisition procedure, whereas a different scanner console may be provided for manipulating, enhancing, and viewing resulting reconstructed images.

As noted above, the scanner console 24 may include one or more computers as well as a monitor 32, allowing images and/or volumes generated from the acquired data to be displayed. These images and/or volumes typically depict internal features of a patient for review and analysis by a technologist or radiologist. To facilitate the review and analysis process, segmentation and extraction of one or more structures of interest may be performed and the extracted structure subsequently displayed.

In structure segmentation, the discrete visualization elements, such as pixels in a two-dimensional image or voxels in a three-dimensional volume, associated with a structure of interest are identified. Once identified, the segmented structure may be extracted and displayed in two-dimensions or visualized in three-dimensions separate from the background image data. Alternatively, the segmented structure may be masked, i.e., subtracted from the image data set, allowing an image or volume to be reconstructed without the segmented structure, which may facilitate the viewing of underlying structures.

Segmentation, however, may be problematic when the image intensities of the structure of interest overlap with the background image intensities, making identification of the structure edges problematic. In addition, non-homogeneities within the structure or background may make accurate identification and selection of structure voxels or voxels difficult. These non-homogeneities may include anatomic or pathologic variability within the patient, such as calcifications or interventional devices, such as stents, in the vasculature. Because of these problems, a technologist may need to initiate aspects of the segmentation process, such as by initially selecting structure starting points, or intervene to prevent early termination of segmentation or improper inclusion or exclusion of background elements into the structure of interest. However, because of the amount of data that must be examined to identify the structure components, typically 150-1,500 slices for CTA data, it is highly desirable to minimize human involvement in the segmentation process, both for time and workload reasons.

Figure 2:
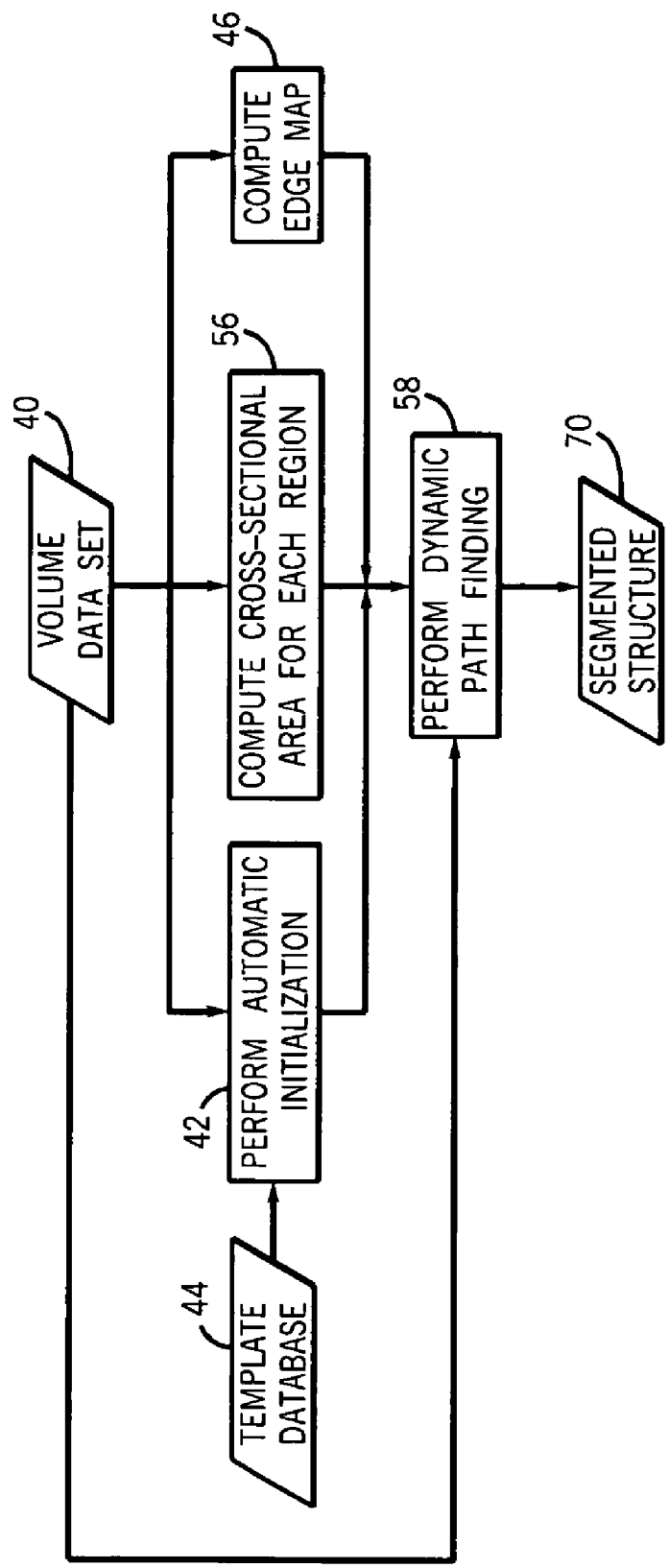
FIG. 2 is a flowchart depicting a technique for dynamically segmenting a structure from a volume data set, in accordance with the present technique.

One technique that may be employed for segmenting structure with reduced or no human intervention is depicted in FIG. 2. The technique depicted in FIG. 2 is modality independent and is therefore applicable to the segmentation of structures within volumes generated by a variety of modalities, including CT, MR, PET, EBT, and so forth. For the sake of simplicity, the technique is discussed in the context of CTA, however, as one of ordinary skill in the art will appreciate, the technique may be applied to other modalities and other structures.

In the context of a CTA example, the volume dataset 40 may be a reconstructed stack of axial slices, typically formatted in the Digital Imaging and Communications In Medicine (DICOM) standard. The in-plane resolution of the data varies may be between 0.55 mm and 0.88 mm with a reconstructed slice thickness range of 1.25 mm to 2.0 mm, though other in-plane and in-z resolutions are possible. The image resolutions in each of the three dimensions may be recorded to help in monitoring and assessing information about structures in an exact physical measure. The image intensities associated with each slice may conform to a standard 16-bit brightness value.

An automatic initialization step 42 may be performed on the volume of interest to generate initial or seed points for three-dimensional structure tracking. In particular, the automatic initialization step 42 locates three-dimensional structures of interest in the volume 40 without manual input. The automatic initialization step 42 may identify the three-dimensional objects using simple or fundamental two-dimensional or three-dimensional geometric representations such as cross sections, projections, and so forth, and/or using functional models such as intensity distribution, intensity level, pattern, and so forth. By using geometrical and functional templates, the automatic initialization algorithm may be generalized to identify three-dimensional structures of interest from any volume dataset, regardless of the underlying imaging modality.

A template database 44 may provide templates to the automatic initialization step 42. The template database 44 may contain various templates based on objects of interest and the possible intensity distributions of such objects. Each template is a basic representation of an object that captures geometric and/or functional characteristics of the object. For example, in the CTA context the structure of interest is the three-dimensional vascular network, which is comprised of essentially tubular components. A suitable geometrical template for vasculature, therefore, may include a round template model since blood vessel cross-sections are generally circular in axial, coronal, sagittal, or arbitrary oblique planes of a dataset. Similarly, a suitable functional template for vasculature may include low standard deviations of intensities or some other statistical homogeneity criteria, since radio-opaque dyes or contrast agents used for CTA typically provide uniform X-ray attenuation. If desired, customized template models can be created for objects of interest depending on the application. In the CTA example, therefore, a template driven automatic initialization step 42 may be used to locate regions of the volume dataset 40 that substantially match the template characteristics, i.e., round regions having uniform intensity. These located regions indicate regions of vasculature, i.e., the structure of interest, and serve as potential starting or seed points for further structure identification and segmentation.

In addition to the starting points, the edges of the structure of interest may be determined such as by locating areas or regions with strong intensity contrast. The edge locations may be used to generate an edge map, as depicted at step 46, indicative of object boundaries within the image data. For example, gradient edge detection is often used to detect object boundaries, since edges correspond to strong illumination gradients. In the present technique, as depicted in FIG. 3, the gradient at a voxel may be calculated at step 48 by finding the maximum absolute gradient component of the voxel relative to the twenty-six adjacent voxels. Determining the gradient for each voxel relative to each of the twenty-six adjacent voxels allows weak boundaries, which might otherwise be missed, to be detected.

Once the gradient of each voxel is determined, a gradient image 50 may be generated which represents the gradient associated with each voxel. A threshold, which may be provided by the operator or statistically determined from the image data, may be applied at step 52 to determine which voxels constitute edge voxels based upon their corresponding gradient values. An edge map 54 may be generated depicting the edge voxels. The edge map 54 prevents subsequent structure identification and segmentation algorithms from erroneously including voxels from background regions and adjacent objects in the segmented structure.

The next step in segmentation is a dynamic path finding step 58, described in greater detail in FIG. 4, which extracts three-dimensional structures of interest from the volume dataset 40 starting from the seed voxels computed by the automatic initialization step 42. The dynamic path finding step may take the edge map 46, the seed voxels, and the cross sectional sizes of the identified regions, computed at step 56, as inputs for constrained region growing. The dynamic path finding operation is typically an iterative process in which the regions identified by automatic initialization comprise the original seed voxels 60 that form the initial foreground region. The foreground region is iteratively grown in all the directions to extend the region in three-dimensions.

All voxels connected to the seed voxels 60 comprise a queue of candidate voxels 64. The candidate voxels are merged with the foreground region, as depicted at step 62, if the candidate voxels meet the desired constraint, such as a desired homogeneity criterion. Candidate voxel which are merged with the growing region become the new seed voxels 60 and the candidate voxel queue is updated to reflect the latest set of connected voxels, as depicted at step 66. Region growing may be continued a configured number of iterations or until the candidate voxels queue is emptied, as determined at decision block 68, or substantially emptied. Once region growing is terminated, the merged voxels comprise the segmented structure 70.

As noted above, the growing process may be dynamically altered. In particular, the constraint, used in the path finding step 58 may be dynamically altered based on anatomy or local statistics of the three-dimensional structure. In this manner, the constraint may be modified to allow the path finding process to properly segment non-homogeneous three-dimensional structures. Path tracking, therefore, may be altered based on the anatomy of the structure.

For example, the constraints used for path finding may be dynamically changed based on size of the cross section and local statistics of the region. In particular, the size of the cross section of each region, as determined at step 56, may indicate whether the region is isolated from the background object or connected with the background structures. Sudden change in size of the cross section may indicate merging and splitting of the three-dimensional structures in the volume dataset 40. For example, in the case of CTA, a region size less than 30 mm$^2$ suggests that the cross-section of the three-dimensional vascular structure is isolated from the background structures. Constraints on region growing may therefore be relaxed for candidate voxels associated with these regions. A region size greater than 30 mm$^2$ suggests that the cross section of the three-dimensional vascular structure is connected with the background structures, such as bone. Constraints on the region growing may therefore be tightened for candidate voxels associated with these regions. The edge map 54 prevents the region growing process growing into connected non-vascular structures.

The constrained growth of the foreground region may be demonstrated by the following possible rules:

1. If a candidate voxel belongs to a region that is smaller than a low size threshold ($ST_{small}$), the candidate voxel may be merged with the foreground region, i.e., the segmented structure, if its intensity lies between a low intensity threshold ($T_{low}$) and a high intensity threshold ($T_{high}$). The thresholds $T_{low}$ and $T_{high}$ represent the range of the intensity distribution of the foreground region. The various thresholds may be calculated from the initial starting points, i.e., seed voxels 60. If a candidate voxel is merged with the foreground region, unmerged voxels connected to the merged voxel are added to the candidate voxel queue 64 for the next iteration of constrained growth.

2. If a candidate voxel belongs to a region that is larger than $ST_{small}$, the candidate voxel may be merged with the foreground region if the intensity difference between the candidate point and the connected voxel in the foreground region is less than $0.6*\sigma_a$. The standard deviation $\sigma_a$ represents the standard deviation of the classified voxels in a local cube of size n*n*n around the seed voxels 60. The initial value of $\sigma_a$ is calculated from the starting seed voxels 60, prior to iterative growth. If a candidate voxel is merged with the foreground region, unmerged voxels connected to the merged voxel are added to the candidate voxel queue 64 for the next iteration of constrained growth.

As noted above, during the iterative process, voxels classified as structure in one iteration, i.e., merged voxels, become the seed voxels 60 for the next iteration. At the end of each iteration, $\sigma_a$ may be updated to revise the local statistics of the region. The adaptive parameter $\sigma_a$ is calculated in a local cube of dimension n*n*n around the seed voxels 60. The variable n is typically a whole number between 1 and 10, for example, n may equal 6 in a typical CTA application. By dynamically constraining growth based upon the iteratively updated parameter $\sigma_a$ the tracking of non-homogeneous structures may be enhanced.

As will be appreciated by those of ordinary skill in the art, the preceding examples represent but one set of possible rules which allow for dynamic modification of the of the constrained growth process. The rules may be modified or other rules developed to customize the rules to specific anatomical regions based upon the characteristic and properties of the anatomical region. Similarly, the rules may be modified or other rules developed based on the modality employed to generate the volume dataset 40.

The present technique may be implemented as one or more computationally efficient routines, allowing for the automatic segmentation of structure in a volume dataset. Due to the automated nature and computational efficiency of the segmentation process, the segmented structure may be obtained in a near-real time, or a real time manner. Likewise, the robustness of the technique makes it useful for processing any data sets regardless of the presence or absence of pathologies or of the imaging modality used to generate the volume dataset 40.

The segmented structure 70, once obtained may be extracted and viewed separately from the background image data or masked to improve the view of the background image data. Alternatively, the segmented structure 70 may be visualized at varying degrees of opacity and translucence, such that the technologist may fade the segmented structure 70 in and out of the volume rendering. In this manner, the technologist may use the presence of the segmented structure 70 to provide orientation and location information. Once oriented, however, the segmented structure 70 may be excluded to examine other structures or background. In addition to configuring the translucence or opacity of the mask, the technologist may be provided with the ability to increase or decrease the intensity of the segmented structure in an image or volume, in order to generate the desired rendering.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for segmenting a Structure, comprising the steps of:
   iteratively merging one or more candidate voxels into a foreground region comprising at least one or more seed voxels, wherein the candidate voxels are merged based on one or more dynamic constraints and wherein the merged candidate voxels become the seed voxels for the next iteration;
   iteratively updating a queue of candidate voxels each iteration based upon the new seed voxels; and terminating the iterative processes to generate a segmented structure comprising the foreground region;
wherein at least one of the dynamic constraints is updated based on at least one of a cross section of the region and a local statistic of the region.

2. The method as recited in claim 1, wherein terminating the iterative process occurs when the queue of candidate voxels is substantially empty.

3. The method as recited in claim 1, further comprising selecting an initial set of seed voxels using one or more templates.

4. A computerized method for segmenting a structure, comprising the steps of:
iteratively merging one or more candidate voxels into a foreground region comprising at least one or more seed voxels, wherein the candidate voxels are merged based on one or more dynamic constraints and wherein the merged candidate voxels become the seed voxels for the next iteration;
iteratively updating a queue of candidate voxels each iteration based upon the new seed voxels; and
terminating the iterative process to generate a segmented structure comprising the foreground region;
wherein the step for iteratively merging updates at least one of the dynamic constraints based on at least one of a cross section of the region and a local statistic of the region.

5. The computer program, as recited in claim 4, wherein the step for termination terminates the iterative processes when the queue of candidate voxels is substantially empty.

6. The computer program as recited in claim 4, further comprising a step for selecting an initial set of seed voxels using one or more templates.

7. An imaging system, comprising:
an imager configured to generate a plurality of signals representative of one or more structures within a volume of interest;
data acquisition circuitry configured to acquire the plurality of signals;
data processing circuitry configured to process the plurality of signal, wherein the
data processing circuitry is further configured to iteratively merge one or more candidate voxel into a foreground region comprising at least one or more seed voxels, wherein the candidate voxels are merged based on one or more dynamic constraints and wherein the candidate voxels are merged based on one or more dynamic constraints and wherein the merged candidate voxels become the seed voxels for the next iteration, to iteratively update a queue of candidate voxels each iteration based upon the new seed voxels, and to terminate the iterative process to generate a segmented structure comprising the foreground region;
system control circuitry configured to operate at least one of the imager and the data acquisition circuitry; and
an operator workstation configured to communicate with the system control circuitry and to receive the plurality of signals from the data processing circuitry;
wherein the data processing circuitry updates at least one of the dynamic constraints based on at least one of a cross section of the region and a local statistic of the region.

8. The imaging system as recited in claim 7, wherein the data processing circuitry terminates the iterative processes when the queue of candidate voxels is substantially empty.

9. The imaging system as recited in claim 7, wherein the data processing circuitry is further configured to select an initial set of seed voxels using one or more templates.

10. An imaging system, comprising:
means for iteratively merging one or more candidate voxels into a foreground region comprising at least one or more seed voxels, wherein the candidate voxels are merged based on one or more dynamic constraints and wherein the merged candidate voxels become the seed voxels for the next iteration;
means for iteratively updating a queue of candidate voxels each iteration based upon the new seed voxels; and
means for terminating the iterative processes to generate a segmented structure comprising the foreground region;
wherein the data processing circuitry updates at least one of the dynamic constraints based on at least one of a cross section of the region and a local statistic of the region.

11. A method for automatically segmenting a structure from a set of image data, comprising the steps of:
selecting one or more initial regions corresponding to a structure of interest from a volume data set;
generating an edge map from the volume data set; and
iteratively segmenting the structure of interest using at least the one or more initial regions and the edge map, wherein the segmentation is based upon one or more dynamic constraints;
wherein iteratively segmenting the structure of interest comprises;
iteratively merging one or more candidate voxels into a foreground region comprising at least one or more seed voxels, wherein the candidate voxels are merged based on the one or more dynamic constraints and wherein the merged candidate voxels become the seed voxels for the next iteration;
iteratively updating a queue of candidate voxels each iteration based upon the new seed voxels; and
terminating the iterative processes to generate a segmented structure comprising the foreground region;
wherein at least one of the dynamic constraints is updated based on at least one of a cross section of the region and a local statistic of the region.

12. The method as recited in claim 11, wherein generating the edge map comprises:
calculating a gradient for each of a plurality of voxels of the volume data set by determining a maximum absolute gradient component relative to each adjacent voxel; and
identifying one or more edge voxels from the plurality of voxels based upon a comparison of the gradients of each of the plurality of voxels to a threshold edge gradient.

13. The method as recited in claim 11, wherein terminating the iterative processes occurs when the queue of candidate voxels is substantially empty.

14. The method as recited in claim 11, further comprising selecting an initial set of seed voxels using one or more templates.

15. The method as recited in claim 11, wherein selecting one or more initial regions comprises:
providing at least one of a geometrical template and a functional template, wherein each template represents at least one characteristic of the structure of interest; and identifying one or more regions of the structure of interest based upon the similarity of the respective characteristic in the regions and the provided templates.

16. The method as recited in claim 15, wherein the geometrical template comprises a geometrical shape.

17. The method as recited in claim 15, wherein the functional template comprises at least one of a statistical homogeneity criteria, an intensity distribution, an intensity level, and a pattern.

18. A computerized method for automatically segmenting a structure from a set of image data, comprising the steps of:
selecting one or more initial regions corresponding to a structure of interest from a volume data set;
generating an edge map from the volume data set; and
iteratively segmenting the structure of interest using at least the one or more initial regions and the edge map, wherein the segmentation is based upon one or more dynamic constraints;
wherein the routine for iteratively segmentation the structure of interest iteratively merges one or more candidate voxels into a foreground region comprising at least one or more seed voxels, wherein the candidate voxels are merged based on the one or more dynamic constraints and wherein the merged candidate voxels become the seed voxels for the next iteration, iteratively updates a queue of candidate voxels each iteration based upon the new seed voxels and terminates the iterative processes to generate a segmented structure comprising the foreground region.

19. The computer program as recited in claim 18, wherein the step for generating calculates a gradient for each of a plurality of voxels of the volume data set by determining a maximum absolute gradient component relative to each adjacent voxel and identifies one or more edge voxels from the plurality of voxels based upon a comparison of the gradients of each of the plurality of voxels to a threshold edge gradient.

20. The computer program as recited in claim 18, wherein the step for iteratively segmenting updates at least one of the dynamic constraints based on at least one of a cross section of the region and a local statistic of the region.

21. The computer program as recited in claim 18, wherein the step for iteratively segmenting terminates the iterative processes when the queue of candidate voxels is substantially empty.

22. The computer program as recited in claim 18, wherein the step for selecting identifies one or more regions of the structure of interest based upon the similarity of one or more characteristics of the regions and one or more templates, wherein the templates comprise at least one of a geometrical template and a functional template and wherein each template represents at least one respective characteristic of the structure of interest.

23. An imaging system, comprising:
an imager configured to generate a plurality of signals representative of one or more structures within a volume of interest;
data acquisition circuitry configured to acquire the plurality of signals;
data processing circuitry configured to process the plurality of signals, wherein the data processing circuitry is further configured to select one or more initial regions corresponding to a structure of interest from a volume data set, to generate an edge map from the volume data set, and to iteratively segment the structure of interest using at least the one or more initial regions and the edge map, wherein the segmentation is based upon one or more dynamic constraints, wherein the data processing circuitry generates the edge map by calculating a gradient for each of a plurality of voxels of the volume data set by determining a maximum absolute gradient component relative to each adjacent voxel and by identifying one or more edge voxels from the plurality of voxels based upon a comparison of the gradients of each of the plurality of voxels to a threshold edge gradient;
system control circuitry configured to operate at least one of the imager and the data acquisition circuitry; and
an operator workstation configured to communicate with the system control circuitry and to receive the plurality of signals from the data processing circuitry.

24. The imaging system as recited in claim 23, wherein the data processing circuitry iteratively segment the structure of interest by iteratively merging one or more candidate voxels into a foreground region comprising at least one or more seed voxels, wherein the candidate voxels are merged based on the one or more dynamic constraints and wherein the merged candidate voxels become the seed voxels for the next iteration, iteratively updating a queue of candidate voxels each iteration based upon the new seed voxels, and terminating the iterative processes to generate a segmented structure comprising the foreground region.

25. The imaging system as recited in claim 24, wherein the data processing circuitry is configured to update at least one of the dynamic constraints based on at least one of a cross section of the region and a local statistic of the region.

26. The imaging system as recited in claim 24, wherein the data processing circuitry is configured to terminate the iterative processes when the queue of candidate voxels is substantially empty.

27. The imaging system as recited in claim 23, wherein the data processing circuitry selects one or more initial regions by identifying one or more regions of the structure of interest based upon the similarity of one or more characteristics of the regions and one or more templates, wherein the templates comprise at least one of a geometrical template and a functional template and wherein each template represents at least one respective characteristic of the structure of interest.

* * * * *